(12) United States Patent
Stradella

(10) Patent No.: US 6,397,839 B1
(45) Date of Patent: Jun. 4, 2002

(54) DISPENSING DEVICE FOR FLUID PRODUCT ACTIVATED BY INHALING

(75) Inventor: Giuseppe Stradella, Camogli (IT)

(73) Assignee: Tebro, Luxembourg (LU)

( * ) Notice: Subject to any disclaimer, the term of this patent is extended or adjusted under 35 U.S.C. 154(b) by 0 days.

(21) Appl. No.: 09/623,597

(22) PCT Filed: Mar. 3, 1999

(86) PCT No.: PCT/EP99/01368

§ 371 (c)(1),
(2), (4) Date: Dec. 15, 2000

(87) PCT Pub. No.: WO99/44662

PCT Pub. Date: Sep. 10, 1999

(30) Foreign Application Priority Data

Mar. 4, 1998 (FR) ............................................. 98 02590

(51) Int. Cl.[7] ............................................. A61M 11/00
(52) U.S. Cl. ............................. 128/200.23; 128/200.14; 128/203.12
(58) Field of Search ....................... 128/200.23, 200.14, 128/203.12; 222/402.1, 402.13, 402.23

(56) References Cited

U.S. PATENT DOCUMENTS

| | | | |
|---|---|---|---|
| 3,157,179 A | | 11/1964 | Paullus et al. |
| 3,456,644 A | * | 7/1969 | Thiel ..................... 128/200.23 |
| 3,636,949 A | * | 6/1972 | Kropp ........................ 128/173 |
| 3,789,843 A | * | 2/1974 | Armstrong et al. ......... 128/173 |
| 4,648,393 A | * | 3/1987 | Landis et al. .......... 128/200.23 |
| 5,027,808 A | * | 7/1991 | Rich et al. ............. 128/200.23 |
| 5,031,610 A | * | 7/1991 | Armstrong et al. ..... 128/200.23 |
| 5,060,643 A | | 10/1991 | Rich et al. |
| 5,119,806 A | * | 6/1992 | Palson et al. .......... 128/200.14 |
| 5,217,004 A | * | 6/1993 | Blasnik et al. ......... 128/200.23 |
| 5,507,281 A | | 4/1996 | Kuhnel et al. |
| 5,546,932 A | | 8/1996 | Galli |

FOREIGN PATENT DOCUMENTS

| | | |
|---|---|---|
| EP | 414 536 | 2/1991 |
| GB | 2 292 891 | 3/1996 |
| WO | WO98/52634 | 11/1998 |

* cited by examiner

*Primary Examiner*—John G. Weiss
*Assistant Examiner*—Darwin P. Erezo
(74) *Attorney, Agent, or Firm*—Sughrue Mion, PLLC

(57) ABSTRACT

A dispensing device is disclosed for a fluid product, activated by inhaling, which includes a product reservoir (20), a pump or dosing valve (30), and an activating device controlled by inhaling. The activating device includes a control element (3) and an actuating member (7). The actuating member (7) is urged towards its actuating position when the control element (3) is in its control position. A retaining element (8) is provided, which is mobile between a retaining position and a releasing position. Further provided is a cam element (2), which is urged towards its storing position and is moved into its inhaling position when the user of the device inhales. The retaining element (8) is elastically deformable between its retaining position and its releasing position. The retaining element (8) is urged towards its releasing position by the actuating member (7) when the control element (3) is in its control position.

14 Claims, 4 Drawing Sheets

DISPENSING DEVICE FOR FLUID PRODUCT ACTIVATED BY INHALING

Figure 1:
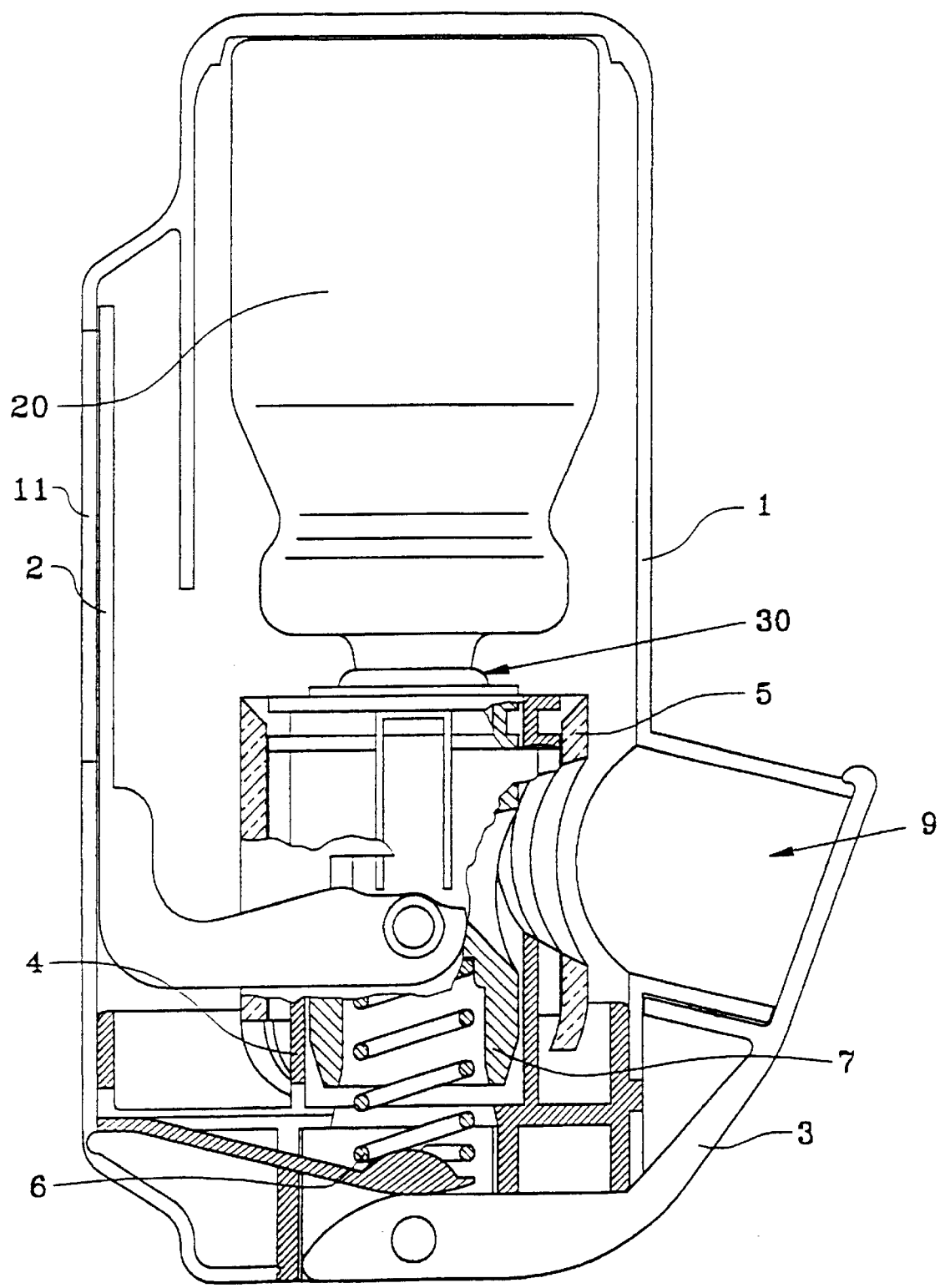

This invention relates to a dispensing device for fluid product activated by inhaling and more particularly, a device of the aerosol type activated by inhaling.

Devices activated by inhaling (generally referred to by the term B.A.I.) are well known in the state of the technology. The main advantage of this type of device is that the dispensing of the product is synchronized with the inhalation of the patient, to guarantee good dispensation of the product. Hence, within the field of aerosol devices, that is to say devices in which the products are dispensed using a propellant gas, numerous types of devices which are activated by inhaling have been proposed. However, all of these devices have the disadvantage of being made up of a large number of components, that is to say, they are complicated and expensive to manufacture and to assemble, which is obviously disadvantageous.

The aim of this invention is to provide a dispensing device for a fluid product activated by inhaling, which functions in a reliable way and which is simple and inexpensive to manufacture and to assemble.

A further aim of this invention is to provide a dispensing device for a fluid product activated by inhaling, which operates in a reliable way and does not require a high degree of aspiration to activate the dispensing of the product.

A further aim of this invention is to provide a dispensing device for a fluid product activated by inhaling, which comprises a product reservoir containing a propellant gas, a pump or dosing valve to selectively dispense the product and an activation device commanded by inhaling, said activation device comprising:

a control element mobile between inoperative and control positions, said control element being displaced by the user, an actuating member, mobile between a non-actuating position, in which the pump or dosing valve is not actuated and an actuating position in which the pump or dosing valve is actuated, said actuating member being urged towards its actuating position when the control element is in its control position, a retaining element, mobile between a retaining position in which it co-operates with the actuating element to retain it in its non-actuating position and a releasing position, in which said actuating member moves into its actuating position, and a cam element, mobile between a storing position in which said retaining element is locked in its retaining position, and an inhaling position, in which said retaining element moves into its releasing position, said cam element being urged towards its storing position and being moved into its inhaling position when the user of the device inhales.

Preferably, the device additionally comprises a locking member that co-operates, on the one hand with the retaining element and on the other hand, with the cam element, said locking member being mobile between a locking position in which it locks said retaining element in its retaining position, and an unlocking position, in which said retaining element moves into its releasing position, said locking member being in the locking position when said cam element is in its storing position, and in the unlocking position, when said cam element is in its inhaling position.

Advantageously, the movement of the control element towards its control position compresses a spring which urges the actuating member towards its actuating position.

Advantageously, the spring is arranged between the control element and the actuating element.

Preferably, the device comprises a casing which receives the reservoir, the pump or dosing valve and the activating device, the casing additionally comprising a dispensing orifice, such as an end mouth-piece through which the user inhales and an opening blocked by the cam element in the storing position.

Advantageously, said cam element is pivotably mounted in the casing, the inhalation by the user creating a pressure drop inside the casing which causes the cam element to pivot towards its inhaling position in which it no longer blocks the opening of the casing.

Advantageously the control element is pivotably mounted on the casing and in its inoperative position, blocks the dispensing orifice of the device.

Preferably, the retaining element is elastically deformable between its retaining position and its releasing position, the retaining element being urged into its releasing position by the actuating member when the control element is in its control position.

Advantageously, the retaining element is housed in a groove of the actuating member, said groove having a slanting side wall which, when the actuating member is urged into its actuating position exerts a force on the retaining element to urge it into its releasing position.

Advantageously, the locking member is a cylindrical sleeve slidably mounted around the retaining element, said sleeve comprising a first part that in the locking position, co-operates with the retaining element to prevent it being moved towards its releasing position and a second part with a larger diameter, that, in the unlocking position, co-operates with the retaining element and enables it to be moved towards its releasing position.

Advantageously the second part of the sleeve is conical so that when the sleeve is brought into its locking position, the conical part of the sleeve co-operates with the retaining element to urge it towards its retaining position.

Preferably, the device additionally comprises a structural element fixed to the casing, the cam element and the control element being pivotably mounted on said structural element.

According to a first advantageous variant, the retaining element is a deformable split ring.

According to a second advantageous variant, the retaining element comprises at least one deformable flexible foot integral with said structural element.

Advantageously, after dispensing the dose of product through the pump or the dosing valve, the control element, when it is brought back into its inoperative position, brings the actuating member back into its non-actuating position so that the retaining element is brought back into its retaining position, the locking member is brought back into its locking position and the cam element is brought back into its storing position.

Figure 2:
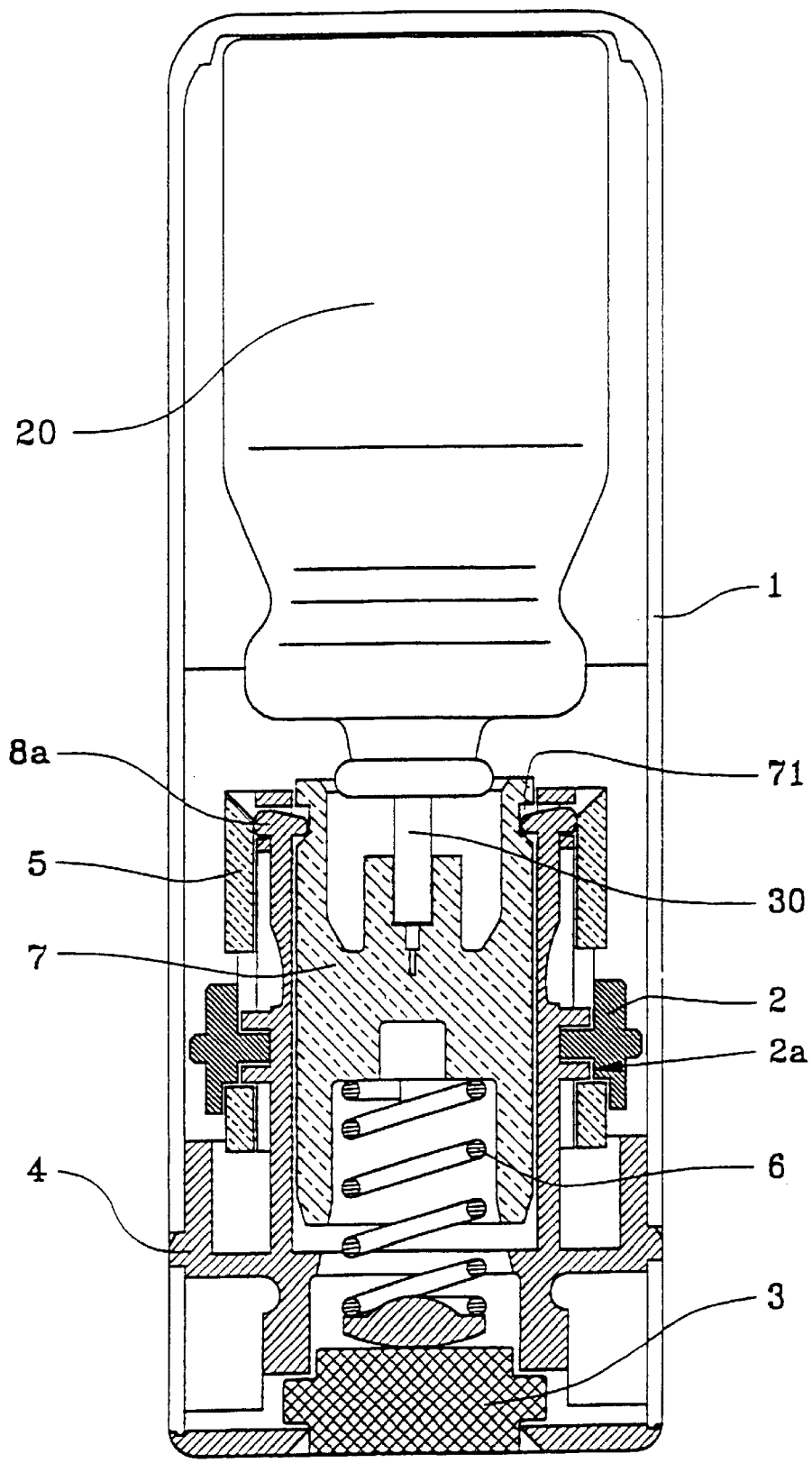
Figure 3:
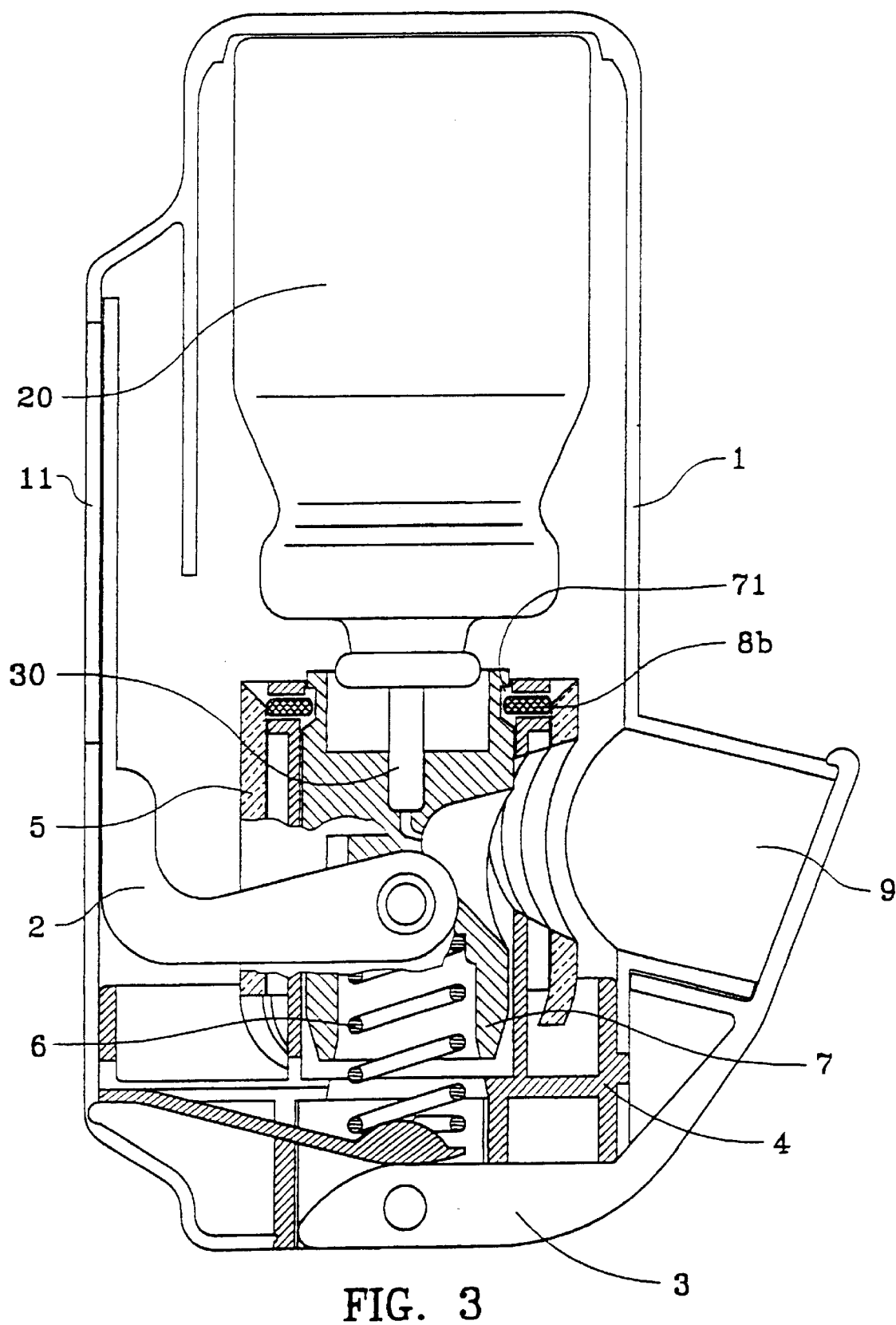
Figures 4, 5:
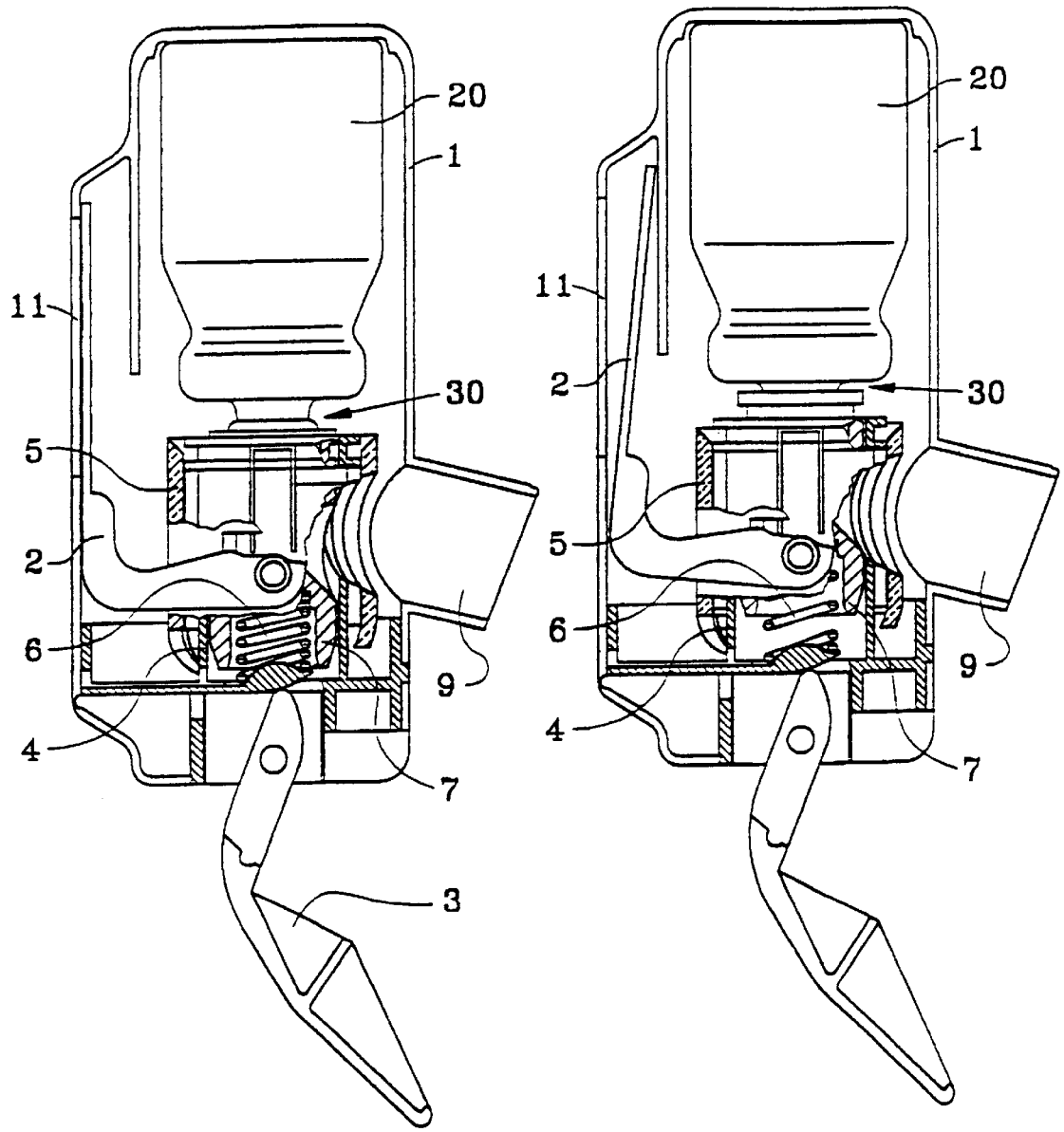

Other features and advantages of this invention will more clearly become apparent during the following detailed description given by way of a non-limitative example, with reference to the attached drawings in which :

FIG. 1 is a diagrammatic section view of a dispensing device according to an advantageous embodiment of this invention in the inoperative position, FIG. 2 is a diagrammatic section view along another section plane representing the device in FIG. 1, also in the inoperative position, FIG. 3 is a view similar to that in FIG. 1, incorporating embodiment variations, also in the inoperative position, FIG. 4 is a view similar to that in FIG. 1, before inhaling, and FIG. 5 is a view similar to that in FIG. 1, after inhaling.

Referring to the drawings, the dispensing device comprises a product reservoir 20, containing the product to be dispensed and a propellant gas, and a pump or dosing valve 30 mounted on said reservoir 20 to selectively dispense the product. The output orifice from the pump or dosing valve 30 is connected via a channel to a dispensing orifice 9, such as an end mouth-piece, through which the user inhales the dispensed product. This dispensing orifice may obviously be created in any manner whatsoever as a function of the desired application for the device. This description will be made with reference to an inhaler comprising a end mouthpiece. However, it is clear that the invention is also applicable to other types of uses, such as, for example, an endonasal treatment.

According to the invention, the device comprises an activating device, controlled by inhalation of the user which is intended to activate the pump or dosing valve 30 when the user inhales through the end mouth-piece 9. Advantageously, the reservoir 20, the pump or dosing valve 30 and the device for actuation by inhaling are contained in a casing 1, which advantageously incorporates the dispensing orifice 9, and on which a control element 3 is mounted which blocks the dispensing orifice 9 in the inoperative position.

According to the invention, this control element 3 is mobile between its inoperative position represented in FIGS. 1, 2 and 3 and a control position represented in FIGS. 4 and 5. Movement of the control element 3 from its inoperative position into its control position has the effect of pre-stressing the activating device, which will subsequently be actuated by inhaling, with, as a consequence, the dispensing of a dose of product through the dispensing orifice 9. To this end, the device for actuation by inhaling comprises a cam element 2 which includes a part, such as a flap which is able to co-operate with an opening 11 provided in the casing 1 of the device. This opening 11 is preferably created in the casing 1 opposite the dispensing orifice through which the user inhales, so that during the inhalation a pressure drop is created inside the casing 1 causing movement of the cam element 2 from a storing position, shown in FIGS. 1, 3 and 4 towards an inhaling position, shown in FIG. 5. The cam element 2 is, when inoperative, urged towards its storing position, but this urging is sufficiently light to be overcome, even by weak inhaling. The device for actuation by inhaling additionally comprises an actuating member 7 which is mobile between a non-actuating position, in which the pump or dosing valve 30 is not actuated, as shown in FIGS. 1 to 4, and an actuating position in which the pump or dosing valve 30 is actuated to dispense a dose of product, as shown in FIG. 5. When the control element 3 is moved towards its control position, the actuating member 7 is urged in the direction of its actuating position. This is preferably done by means of a spring 6 which is suitable for urging the actuating member 7 towards its actuating position. As shown in the Figures, the spring 6 may preferably be arranged between the control element 3 and the actuating member 7. Of course this spring may equally well be provided at another position in the device, for example acting on the reservoir 20 in order to urge it in the direction of the actuating member 7.

The activating device additionally comprises a retaining element 8a, 8b which is able to co-operate with the actuating member 7. This retaining element 8a, 8b is mobile between a retaining position, in which it retains the actuating member 7 in its position of non-actuation, as shown in FIGS. 2 and 3, and a releasing position, in which said actuating member 7 can be moved in the direction of its actuating position, as shown in FIG. 5. This retaining element 8a, 8b is preferably elastically deformable between its retaining position and its releasing position and is urged towards its releasing position by the actuating member 7 which itself is urged towards its actuating position. The retaining element can be created in the form of a split ring 8b, as shown in FIG. 3, or in the form of one or more elastic flexible legs 8a as shown in FIG. 2. Advantageously, the retaining element 8a, 8b is housed in the groove 71 made in the actuating member 7, this groove 71 preferably having a slanting side wall, which has the effect of exerting a radial force on the retaining element 8a, 8b when the actuating member 7 is subjected to an axial force while being urged towards its actuating position.

According to the invention, the cam element 2 in its storing position, is able to lock the retaining element 8a, 8b in its retaining position. When the cam element 2 is moved into its inhaling position, said retaining element 8a, 8b can be moved towards its releasing position so that the actuating member 7 can then be moved towards its actuating position in order to activate the pump or dosing valve 30.

Preferably, the activating device comprises a locking member 5, which may be a sleeve 5, and which co-operates on the one hand, with the retaining element 8a, 8b to lock it in its retaining position while the cam element 2 is in its storing position, and which, on the other hand, co-operates with the cam element 2 so that movement of the cam element 2 towards its inhaling position acts on the locking member 5 to move it from its locking position towards a position for unlocking the retaining element. Advantageously, this locking member 5 is created in the form of a sleeve 5 that is able to slide around the retaining element 8a, 8b in order, when in the locking position, to prevent radial deformation of it towards its releasing position. Preferably, said sleeve 5 comprises a first cylindrical part which, in the locking position, co-operates with the retaining element 8a, and 8b, and a second part of greater diameter which, in the unlocking position, co-operates with the retaining element 8a, 8b to enable it to move by elastic deformation towards its releasing position. Advantageously, this second part of the sleeve 5 is made conical, this particular shape being advantageous, after inhalation of a dose of product, to bring the device for activation by inhaling back into its non-operative position as will be explained below.

Advantageously, the device for activation by inhaling comprises a structural element 4 which is fixed to the casing 1, and on which the control member 3 and the cam element 2 are pivotably mounted as may be seen in FIG. 2. According to an embodiment variant which is shown in FIG. 2, the retaining element can be produced in the form of one or more flexible elastic feet 8a, these being advantageously produced with said structural element 4, as one component. The structural element 4 may possibly comprise a flexible tongue arranged between the control member 3 and the spring 6 to facilitate co-operation between these two components.

The operation of the device according to the invention is as follows.

Before the user wishes to use the device to administer a dose of the product to himself, said device is in the storing position, as shown in FIGS. 1, 2 and 3, in which the control member 3 is in the storing position, blocking the end mouth-piece 9, the actuating member 7 is in the non-operative position and is not being urged in the direction of its actuating position by the spring 6 which is not compressed, the retaining element 8a, 8b being in the retaining position and the locking member 5 in the locking position, while the cam element 2 is in the storing position blocking the opening 11 of the casing. Preferably, the retaining element 8a, 8b is not urged towards its releasing position while the actuating member 7 is not being urged towards its actuating position.

When the user inhales through the end mouth-piece 9, it creates a pressure drop inside the casing 1 which has the effect of causing the cam element 2 to pivot from its storing position shown in FIG. 4, towards its inhaling position, shown in FIG. 5. In particular, the flap part of the cam element 2 is moved away from the opening 11 in the casing 1 to balance the pressure drop created inside the casing. This movement of the cam element 2 from its storing position towards its inhaling position has the effect of causing the locking member 5 to slide axially in relation to the retaining element 8a, 8b. Advantageously, a cam part 2a of the cam element 2 crosses the sleeve 5 and turns in relation to it when the cam element 2 is moved towards its inhaling position, so that said sleeve 5 moves in synchronization with said cam element 2. The retaining element 8a, 8b, under the effect of the force exerted on it by the actuating member 7, is then deformed towards its releasing position which then allows the actuating member 7 to be propelled towards its actuating position by the compressed spring 6 which is acting upon it. The product dose is then expelled through the pump or dosing valve 30 in the direction of the end mouth-piece 9, to be inhaled by the user in a way that is synchronized with his inhaling.

At the end of the inhalation, the user returns the control element 3 to its inoperative position in which it blocks the end mouth-piece 9. This enables the spring 6 to be decompressed and returned to its inoperative position so that the actuating member 7 returns to its non-actuating position with the groove 71 opposite the retaining element 8a, 8b. This then returns to its retaining position, either through its own elasticity, or by being gently assisted by the conical part of the locking member 5 which exerts an inward radial force on said retaining element 8a, 8b, when axially displaced from its unlocking position towards its locking position. The retaining element 8a, 8b therefore returns to its retaining position, the locking member 5 returns to its locking position and the cam element 2 returns to its storing position, so that the device is ready for later use.

This invention therefore provides a fluid product dispensing device activated by inhaling, in which the device activated by inhaling is particularly simple and therefore inexpensive to manufacture and to produce since it comprises a minimum number of constituent items. Hence in its preferred embodiment which is the one shown in the drawings, the activating device comprises six or seven components, namely the control element 3, the structural element 4, the spring 6, the actuating member 7, the retaining element 8a, 8b if it is not produced as one component with the structural element 4, the locking member 5 and the cam element 2. It could even be envisaged that the activating device might be produced with even fewer components, for example by producing the cam element 2 so that it incorporates the locking member 5. This invention therefore allows one to provide a device activated by inhaling that is reliable while at the same time being simple and inexpensive.

What is claimed is:

1. Dispensing device for a fluid product activated by inhaling, which comprises a product reservoir (20) containing a propellant gas, a pump or dosing valve (30) to selectively dispense the product through a dispensing orifice (9), and an activating device controlled by inhaling, said activating device comprising:

a control element (3) mobile between an inoperative position in which it blocks the dispensing orifice (9) and a control position, said control element (3) being displaced by a user, an actuating member (7), mobile between a non-actuating position, in which the pump or dosing valve (30) is not actuated and an actuating position in which the pump or dosing valve (30) is actuated, said actuating member (7) being urged towards its actuating position when the control element (3) is in its control position, a retaining element (8), mobile between a retaining position in which it cooperates with the actuating member (7) to retain it in its non-actuating position and a releasing position, in which said actuating member (7) moves into its actuating position, and a cam element (2), mobile between a storing position in which said retaining element (8) is locked in its retaining position, and an inhaling position, in which said retaining element moves into its releasing position, said cam element (2) being urged towards its storing position and being moved into its inhaling position when the user of the device inhales, characterized in that the retaining element (8) is elastically deformable between its retaining position and its releasing position, the retaining element (8) being urged towards its releasing position by the actuating member (7) when the control element (3) is in its control position.

2. Device according to claim 1, additionally comprising a locking member (5) that co-operates, on the one hand with the retaining element (8) and on the other hand, with the cam element (2), said locking member (5) being mobile between a locking position in which it locks said retaining element (8) in its retaining position, and an unlocking position, in which said retaining element moves into its releasing position, said locking member (5) being in the locking position when said cam element (2) is in its storing position, and in the unlocking position, when said cam element (2) is in its inhaling position.

3. Device according to claim 2, in which the locking member (5) is a cylindrical sleeve slidably mounted around the retaining element (8), said sleeve (5) comprising a first part that in the locking position, co-operates with the retaining element (8) to prevent it being moved towards its releasing position and a second part with a larger diameter, which, in the unlocking position, co-operates with the retaining element (8) and enables it to be moved towards its releasing position.

4. Device according to claim 3, in which the second part of the sleeve (5) is conical so that when the sleeve (5) is brought into its locking position, the conical part of the sleeve (5) co-operates with the retaining element (8) to urge it towards its retaining position.

5. Device according to claim 2, in which, after dispensing the dose of product through the pump or dosing valve (30), the control element (3), when it is returned to its inoperative position, returns the actuating member (7) to its non-actuating position, so that the retaining element (8) is returned to its retaining position, the locking member (5) is returned to its locking position and the cam element (2) is returned to its storing position.

6. Device according to claim 1, in which movement of the control element (3) towards its control position compresses a spring (6) which urges the actuating member (7) towards its actuating position.

7. Device according to claim 6, in which the spring (6) is arranged between the control element (3) and the actuating member (7).

8. Device according to claim 1 a casing (1) that receives the reservoir (20), the pump or dosing valve (30) and the activating device, the casing (1) additionally comprising the dispensing orifice (9), such as an end mouth-piece, through which the user inhales, and an opening (11) blocked off by the cam element (2) in the storing position.

9. Device according to claim 8, in which said cam element (2) is pivotably mounted in the casing (1) inhalation by the user creating a pressure drop in the casing (1) which causes the cam element (2) to pivot towards its inhaling position, in which it no longer blocks the opening (11) of the casing (1).

10. Device according to claim 8, which the control element (3) is pivotably mounted on the casing (1).

11. Device according to claim 8, additionally comprising a structural element (4) fixed to the casing (1), the cam element (2) and the control element (3) being pivotably mounted on said structural element (4).

12. Device according to claim 11, in which the retaining element (8) comprises at least one flexible deformable foot (8*a*) integral with said structural element (4).

13. Device according to claim 1, in which the retaining element (8) is housed in a groove (71) of the actuating member (7), said groove (71) having a slanting side wall which, when the actuating member (7) is urged towards its actuating position, exerts a force on the retaining element (8) to urge it towards its releasing position.

14. Device according to claim 1 in which the retaining element (8) is a deformable split ring (8*b*).

\* \* \* \* \*